(12) United States Patent
Lechot

(10) Patent No.: US 6,979,335 B2
(45) Date of Patent: Dec. 27, 2005

(54) HOLDER FOR SURGICAL REAMER

(75) Inventor: André Lechot, Sous l'Eau-Belle (CH)

(73) Assignee: Precimed SA, Orvin (CH)

( * ) Notice: Subject to any disclaimer, the term of this patent is extended or adjusted under 35 U.S.C. 154(b) by 202 days.

(21) Appl. No.: 10/451,481

(22) PCT Filed: Dec. 21, 2001

(86) PCT No.: PCT/IB01/02675

§ 371 (c)(1),
(2), (4) Date: Jun. 20, 2003

(87) PCT Pub. No.: WO02/49516

PCT Pub. Date: Jun. 27, 2002

(65) Prior Publication Data

US 2004/0116935 A1    Jun. 17, 2004

(30) Foreign Application Priority Data

Dec. 21, 2000 (CH) ................................ 2500/00

(51) Int. Cl.⁷ .......................................... A61B 17/32
(52) U.S. Cl. ................................................... 606/80
(58) Field of Search .................... 606/79–81, 167, 606/170, 180–183; 408/231, 232, 239 R, 408/240; 279/22, 30, 75, 82

(56) References Cited

U.S. PATENT DOCUMENTS

| | | | | |
|---|---|---|---|---|
| 1,160,042 A | * | 11/1915 | Carpenter | 408/156 |
| 2,684,491 A | * | 7/1954 | Roddick | 408/139 |
| 3,219,355 A | * | 11/1965 | Fujinuma | 279/75 |
| 3,521,895 A | * | 7/1970 | Smith | 279/22 |
| 3,633,583 A | | 1/1972 | Fishbein | |
| 3,750,283 A | * | 8/1973 | Hoffman | 30/338 |
| 4,204,692 A | * | 5/1980 | Hoffman | 279/81 |
| 5,199,833 A | * | 4/1993 | Fehrle et al. | 408/239 R |
| 5,222,956 A | | 6/1993 | Waldron | |
| 5,290,315 A | | 3/1994 | DeCarlo, Jr. | |
| 5,316,323 A | * | 5/1994 | Jovanovic | 279/22 |
| 5,398,946 A | * | 3/1995 | Quiring | 279/30 |
| 5,573,255 A | * | 11/1996 | Salpaka | 279/75 |
| 5,575,071 A | * | 11/1996 | Phillips et al. | 30/392 |
| 5,658,290 A | | 8/1997 | Lechot | |
| 5,957,368 A | | 9/1999 | Takebayashi et al. | |
| 5,980,170 A | | 11/1999 | Salyer | |

(Continued)

FOREIGN PATENT DOCUMENTS

DE    1566114 A    10/1970
DE    3934610 A1    4/1991

(Continued)

OTHER PUBLICATIONS

Communication pursuant to Article 96(2) EPC.

Primary Examiner—Eduardo C. Robert
Assistant Examiner—Annette Reimers
(74) Attorney, Agent, or Firm—Moetteli & Associes Sarl; John Moetteli

(57) ABSTRACT

A tool holder for holding a surgical reamer has a head (8) and a retaining device (14, 15). The head has an axis coincident with the axis of rotation of the reamer. The head is provided with at least one radially extending slot (10) receiving a plate (1, 2) of the reamer. The retaining device (14, 15) has a component which engages with a feature of the plate of the reamer. The feature is proximate the axis of rotation of the reamer in order to centrally retain the plate in the slot.

7 Claims, 11 Drawing Sheets

U.S. PATENT DOCUMENTS 6,106,536 A     8/2000   Lechot
6,612,039 B2 *   9/2003   Kakiuchi et al. ............. 30/392

FOREIGN PATENT DOCUMENTS

| | | | |
|---|---|---|---|
| EP | 0704121 | B1 | 11/1995 |
| EP | 0704191 | A1 | 4/1996 |
| EP | 0782890 | A1 | 1/1997 |
| EP | 0893097 | A2 | 1/1999 |
| EP | 0947170 | A2 | 10/1999 |
| FR | 2281025 | | 2/1976 |

* cited by examiner

Fig.2
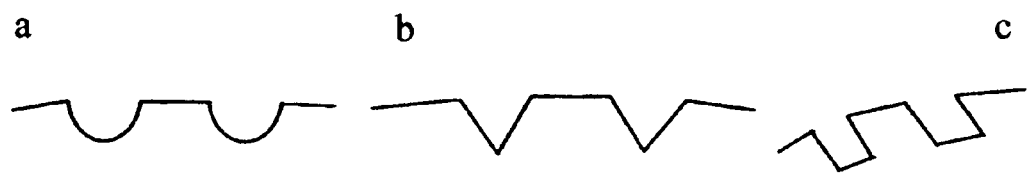
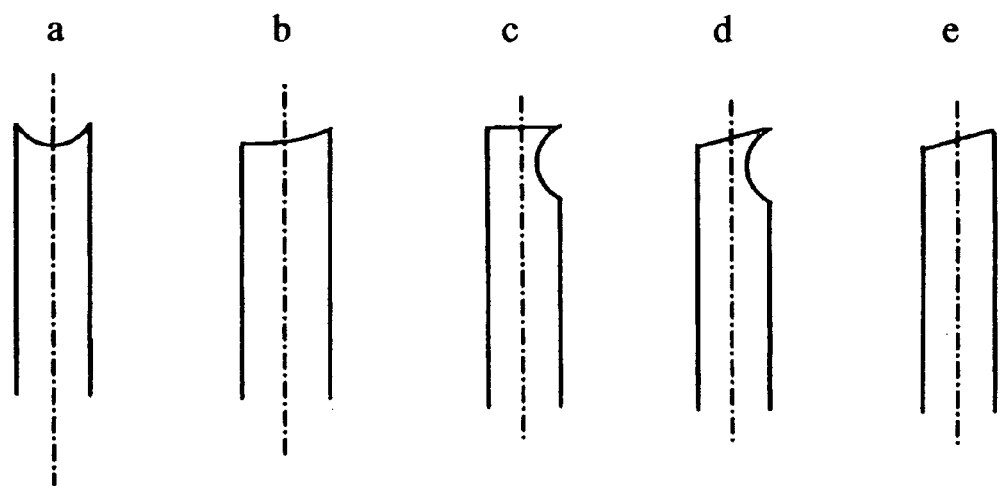
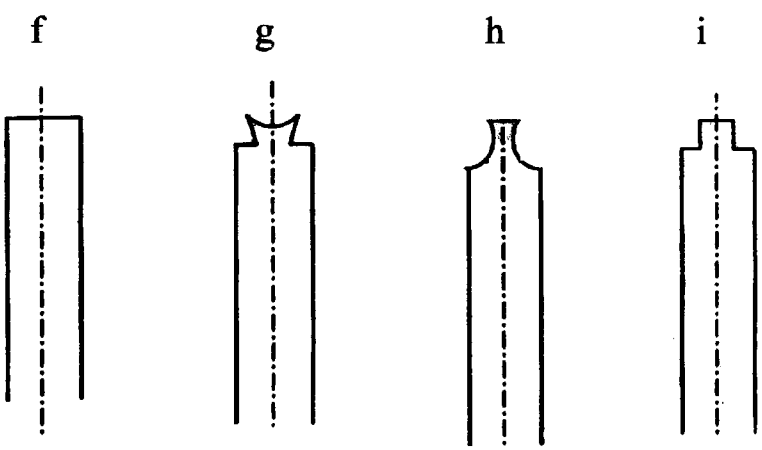
Fig.3

HOLDER FOR SURGICAL REAMER

BACKGROUND OF THE INVENTION

The subject of this invention is a holder for a surgical reamer which drives the reamer in rotation.

A reamer of this sort is known under U.S. Pat. Nos. 3,633,583 and 5,290,315. On these reamers, the cutting edge is formed on a half-disk inserted into a diametric split made in a monolithic head which is noticeably hemispherical. The disk is held in the head by a screw and the head has gashes, like a drill bit, for the formation of shavings. In operation, there is an increased risk of these reamers becoming off centre due to the lack of homogeneity of the osseous matter. In addition, an incision must be relatively large to receive this reamer.

From document EP 0 947 170, the content of which is incorporated herein by reference, a surgical reamer is shown, particularly intended for the processing of the cotyloid cavity when replacing the hip joint with a total prosthesis, in the shape of a revolving hollow body, in particular a hemispherical cap stretching from one side of the rotary axis and whose edge, over half of its circumference, constitutes the cutting edge. The surface of the cap itself may be fitted with teeth as with reamers of the rasp type which are commonly seen in previous practice, as described, for instance, in patents FR 2 281 025, EP 0 704 121 and 0 782 890, the content of which is incorporated herein by reference. However, it is very difficult to form an exact hemisphere using the usual processes, such as stamping. Further, the static profile area is large, thus making the reduction of the holder size a moot issue.

What is needed is a holder for a surgical reamer allowing the centring to be maintained whilst in operation, using simple means. In addition, what is needed is a reamer holder that has a small insertion profile, compared to the swept cutting area of the reamer.

SUMMARY OF THE INVENTION

A tool holder is provided for holding a surgical reamer. The tool holder has a head and a retaining device. The head has an axis coincident with the axis of rotation of the reamer. The head is provided with at least one radially extending slot receiving a plate of the reamer. The retaining device has a component which engages with a feature of the plate of the reamer. The feature is proximate the axis of rotation of the reamer in order to centrally retain the plate in the slot. The reamer to which the holder engages has a cutting structure rotatable about a longitudinal axis. The structure has a static profile area upon insertion of the reamer into the bone socket and a dynamic profile area generated upon rotation, both profile areas lying transverse to the axis. The static profile area is substantially smaller than the dynamic profile area. Therefore, to benefit from this small profile area, the holder must also have a small profile area. Due to the reamer having centrally located holes (18), the holder may be affixed to it in a location central to the axis of rotation. The invention therefore has a low insertion profile permitting entry into an incision of a relatively small size.

The reamer form may be spherical, conical or of some other shape. At least one cutting edge can be fitted with teeth.

According to the preferred mode of production for the invention, the reamer is made up of two plates which are split down the middle according to their axis of symmetry and housed at right angles to and inside one another. This is particularly simple to manufacture and also stands out due to its good rigidity and by how easy it is to clean.

The plates constitute the cutting structure. The plates are angularly arranged around the rotary axis in such a way as to form three edges including at least one which is a cutting edge. The distribution of at least three edges around the rotary axis ensures that centring is maintained during milling. If only one of the edges is a cutting edge, the other edges are used only for guiding, that is to say for maintaining the centring.

The disk, whose split leads out onto the top of the reamer, can usefully be cut so as to release the profile of the other disk at the top and thus allow a cut in the centre when milling.

The plates have holes used for fixing the reamer onto the tool holder with a head fitted with frontal slots extending radially in relation to the support axis and oriented in such a way as to allow them to receive the reamer plates. The devices used to hold the reamer in the slots may be made up of balls which engage in the holes on the reamer's plates and a ball locking device keeping the balls engaged in the holes in the plates.

BRIEF DESCRIPTION OF THE DRAWINGS

As an example, the appended drawing shows a mode for producing the invention.

FIGS. 2a–2c shows three examples of teeth farmed on the disks.

FIGS. 3a–3i shows examples of disk cutting profiles.

DETAILED DESCRIPTION OF THE INVENTION

Figure 1:
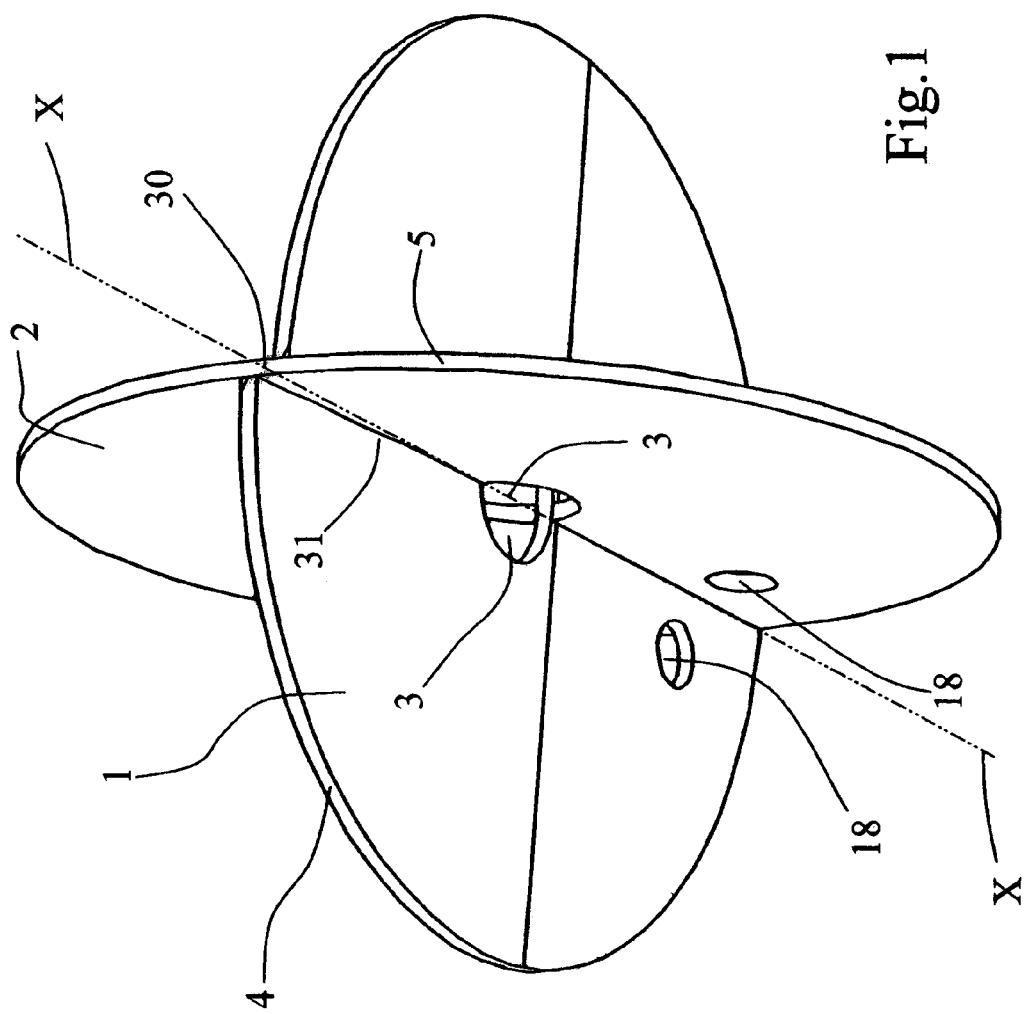
FIG. 1 is a perspective view of the reamer.

The holder of the invention is particularly adapted for holding a particular reamer, as shown in FIG. 1. This reamer is made up of two disks or plates 1 and 2 perpendicularly assembled. The plates 1 and 2 make up a cutting structure 50. The cutting structure 50 is rotatable about a longitudinal axis X—X when mounted to a holder 6.

For this purpose, the plates are split down the middle, that is to say according to a radius leading into a central circular cut 3 and they are housed in one another by means of these slots and laser welded so as to give a spherical case of which edges 4 and 5 make up meridians. Edges 4 and 5 present sharp edges forming cutting edges.

In the example shown, disk 1 has a split which leads to the top 30 of the reamer and is cut so that the sides of its split 31 diverge from one another on the plane of the other disk 2, on both sides of the reamer's rotary axis X—X. The effect of this is to release the edges of the disk 2 at the top 30 and to thus allow a centre cut when milling.

At least one of the edges 4, 5 of the plates can be fitted with cutting teeth. Examples of teeth shapes are shown in FIG. 2, either teeth in a U shape (a), an "N" shape (b) or sloping slot teeth (c). The four edges of the reamer should preferably be fitted with teeth and these teeth are offset, respectively alternated, from one disk to the other or from one half-disk to the next, in relation to the trajectory of these teeth, so as to obtain a full sweep, without grooves, when milling a spherical cavity.

The cutting edges 4 and 5 may show various cutting profiles examples of which are shown in FIG. 3
  a) half-moon profile on the topside,
  b) elliptical profile generating a positive cut,
  c) half-moon profile on the cutting side of the plates with a neutral cutting angle
  d) half-moon profile on the cutting side of the plates with a positive cutting angle
  e) diagonal profile generating a positive cutting angle,
  f) neutral profile,
  g) half-moon profile on the topside with two relief angles per disk,
  h) half-moon profile on both sides of the plates,
  i) tenon profile which can synthesise profiles a} to h}.

A reamer of this sort cannot be fixed directly onto a prior art tool holder as described in the applicant's patent EP 0 704 191 (U.S. Pat. No. 5,658,290), the content of which is incorporated by reference herein, which has a head intended to house a cross help by a bayonet fixture. In order to be able to use the same tool holder for reamers fitted with a fixing cross, the new reamer if fixed onto a holder 6 shown in FIGS. 4 to 8. In the drawings, the holder is shown as a holder to a prior art tool holder but for the sake of this application, is considered a holder in and of itself and is therefore referred to as such.

Such an interface is suitable for connecting to the tool holder described in Applicant's incorporated U.S. Pat. No. 5,658,290.

The holder 6 has a cylindrical body 7 fitted, at one end, with a head 8 designed to house the reamer and, at the other end, with a fixing cross interface made up of four cylindrical branches 9 forced radially through the body 7. Such an interface is suitable for connecting to the tool holder described in Applicant's incorporated U.S. Pat. No. 5,658, 290. The head 8, generally cylindrical in shape, is split diametrically so as to have four slots 10 which are at right angles to one another, whose width corresponds to the thickness of plates 1 and 2. These slots 10 are limited on one side by a relatively thin wall 11 and, on the other side, by a rather thicker wall 12. The walls 12 are pierced by a circular hole 13, which is cylindrical over most of the walls. The balls 14, whose diameter is greater than the thickness of the walls 12 are held in these holes. These balls 14 can also be moved into the holes 13 so as to release the slots 10 or not.

Figure 7:
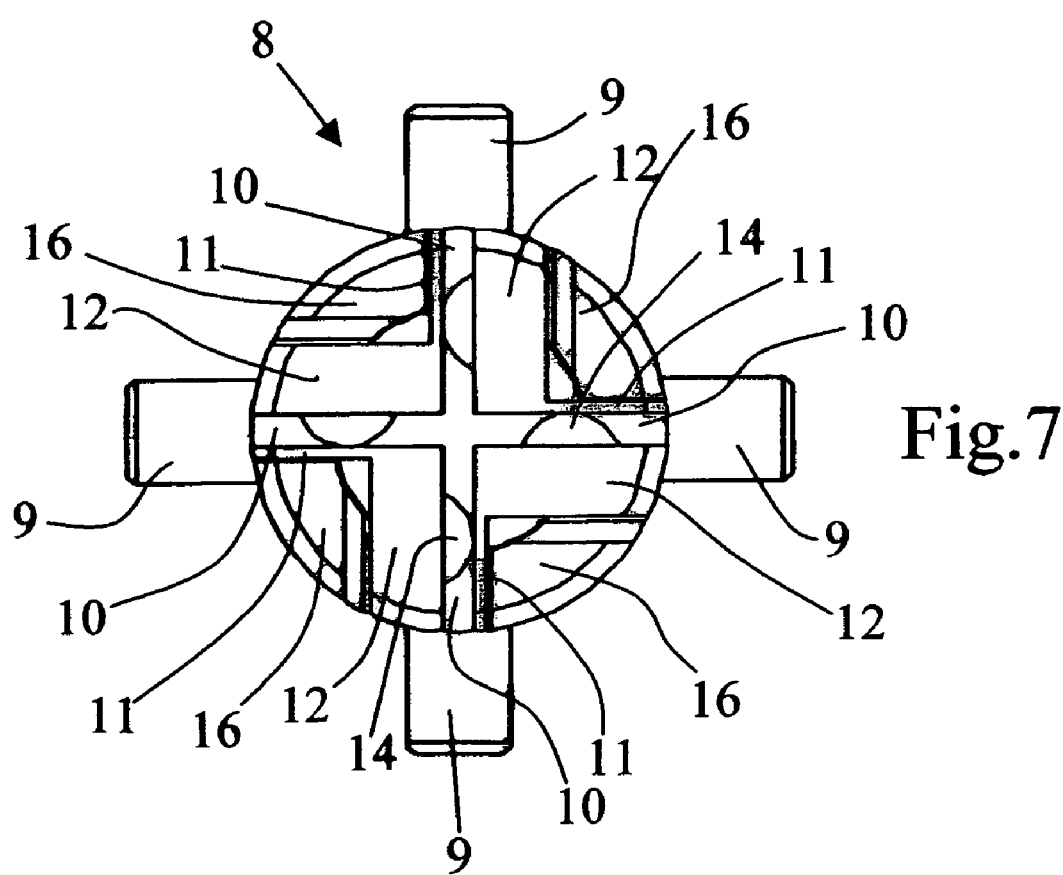
FIG. 7 is an axial view of the adapter.
Figure 8:
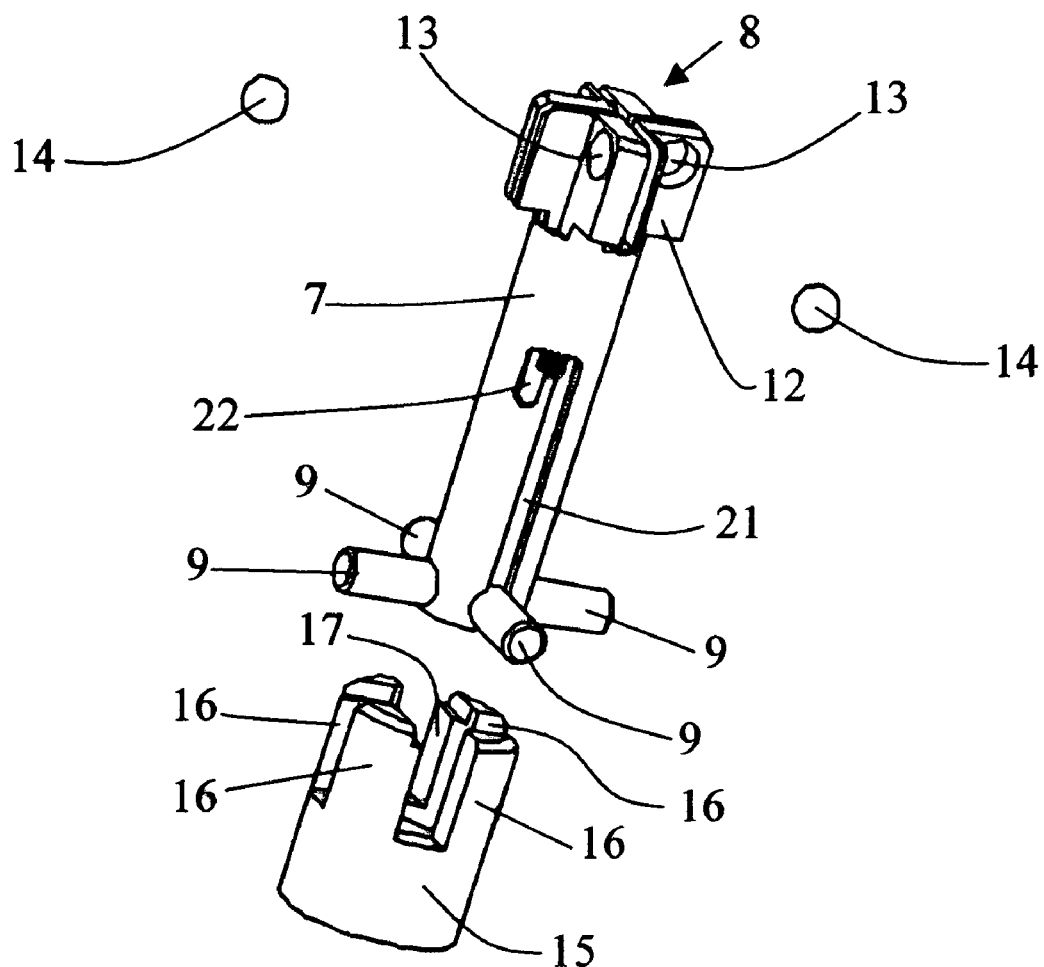
FIG. 8 is an exploded view of the adapter.

A locking ring 15, with four pins 16 is mounted, sliding, onto the body 7 stretching out in parallel to the axis of the ring. These pins 16 are engaged in the head 8, more precisely in the spaces left free by the walls 11 and 12. Each of these pins 16 has one flat side 17 which at least approximately slides onto the side of a wall 12 opposite the corresponding split 10, so as to keep the corresponding ball engaged in the split 10, as shown in FIG. 7. If the reamer is engaged in the slots 10, the balls 14 are then engaged in the holes 18 on plates 1 and 2 so that the reamer is held onto the head 8.

Figure 4:
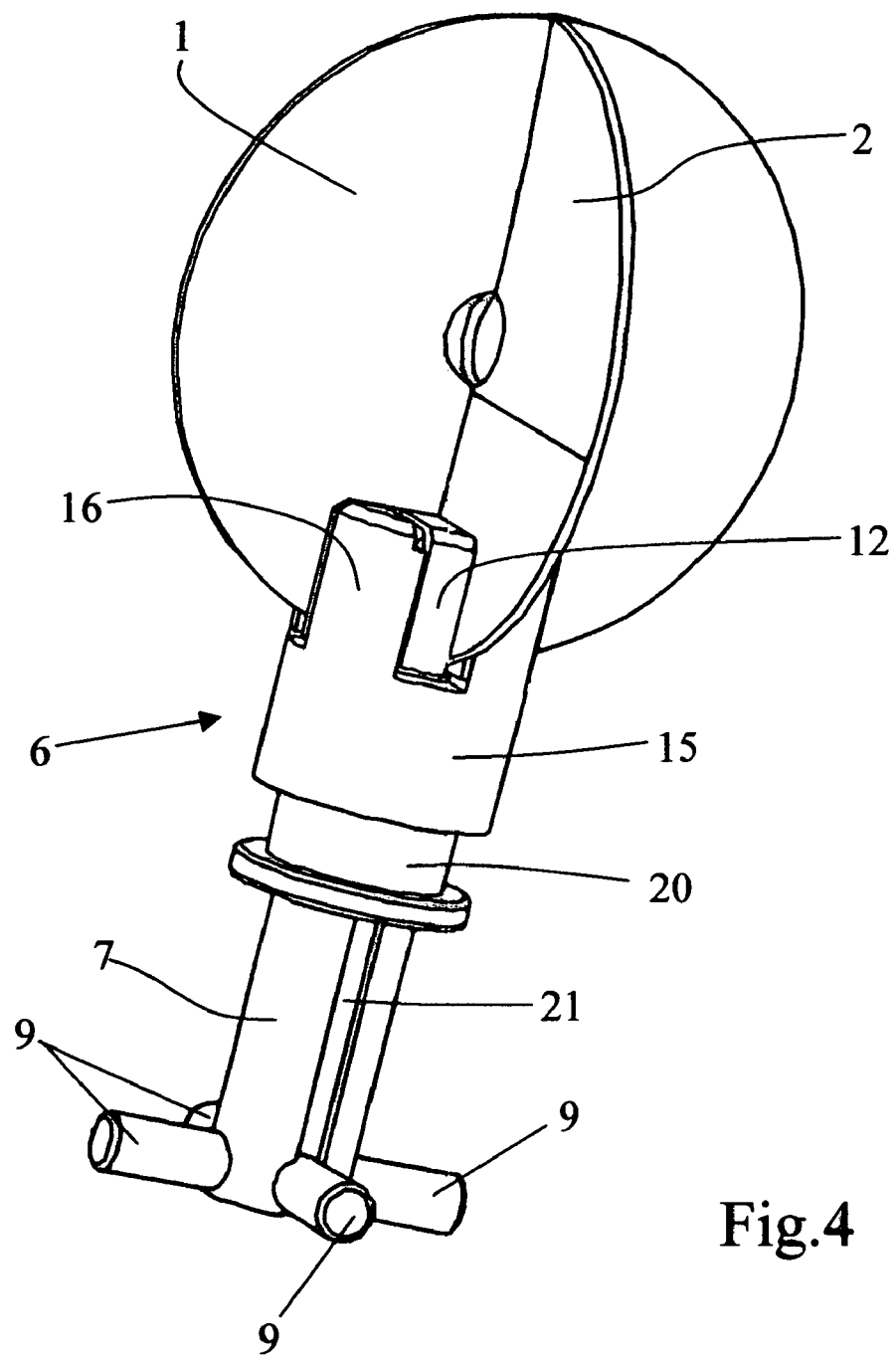
FIG. 4 shows the same reamer mounted on an adapter.
Figure 5:
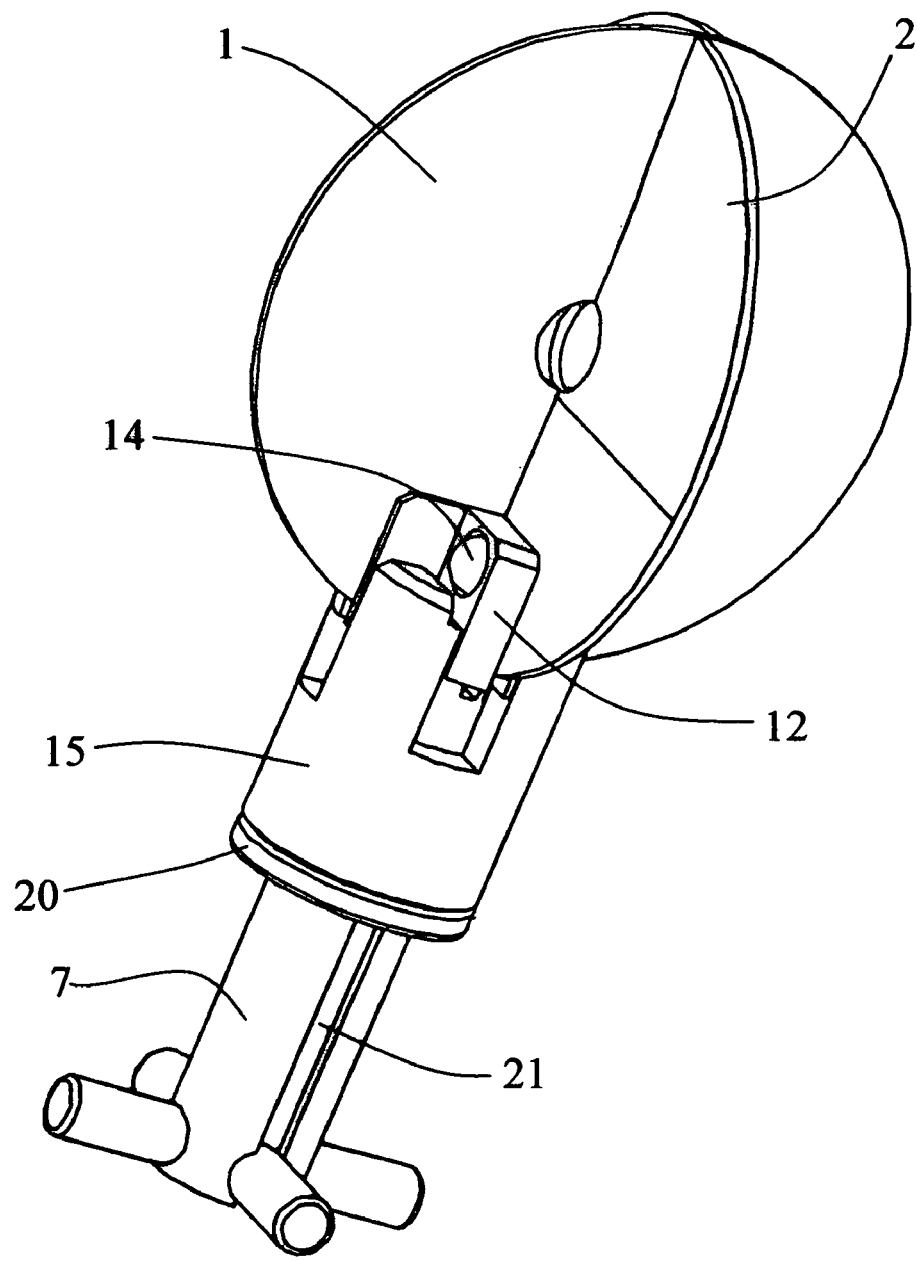
FIG. 5 shows the adapter in the reamer release position.
Figure 6:
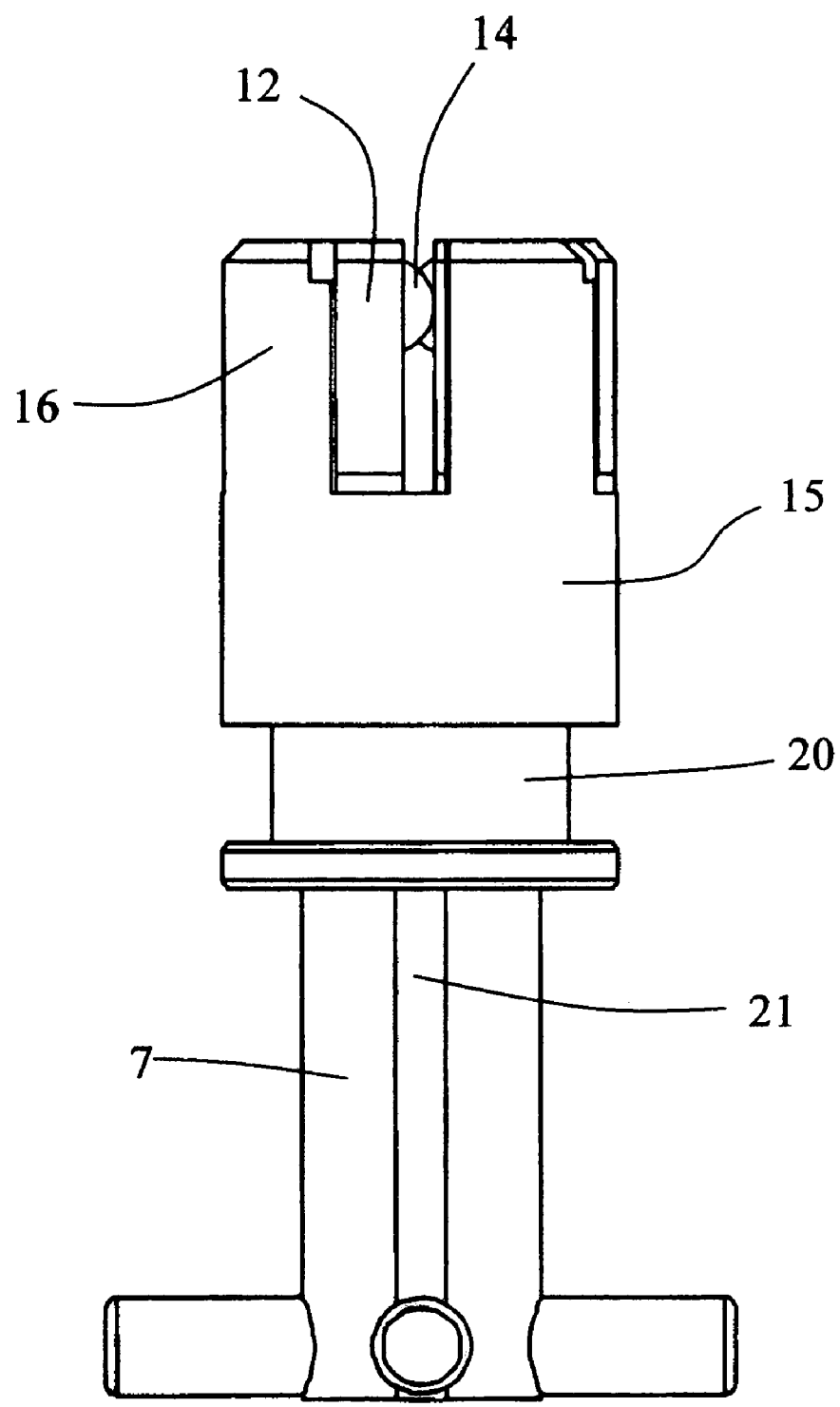
FIG. 6 is a side view of the adapter.

The ring 15 is held in this locking position by a spring 19 which rests on a supporting ring 20 which is mounted on the body 7 of the holder, as shown in FIG. 4. In order to release the reamer all that must be done is pull out the locking ring 15 by constricting the spring 19, as shown in FIG. 5. The reamer can then be removed from the head 8 by pushing back the balls 14. The same method is used to fix the reamer onto the holder. This type of locking/unlocking mode is described in the Swiss patent application No 409/00, the content of which is incorporated by reference herein. To lock the balls 14 into the reamer, all you have to do is release the ring 15.

In order to allow the adapter to be cleaned properly, the supporting ring 20 is mounted in such a way that it can be pulled out backwards as far as the cylindrical branches 9, which allows you to also bring back the locking ring 15 and to release the spring on the ring 15. For this purpose, the supporting ring 20 is fitted with a radial pin directed internally (not shown in the drawing) and the body 7 of the adapter has a longitudinal groove 21 into which this pin can slide. The upper end of the groove 21 leads to a notch 22 into which the pin on the ring 20 can be bayonet fixed by means of a slight rotation.

The reamer can usefully be fitted with a device allowing the shavings to be recovered. The plates offer a particularly simple and effective solution shown in FIGS. 9a, 9b and 10.

Figure 9:
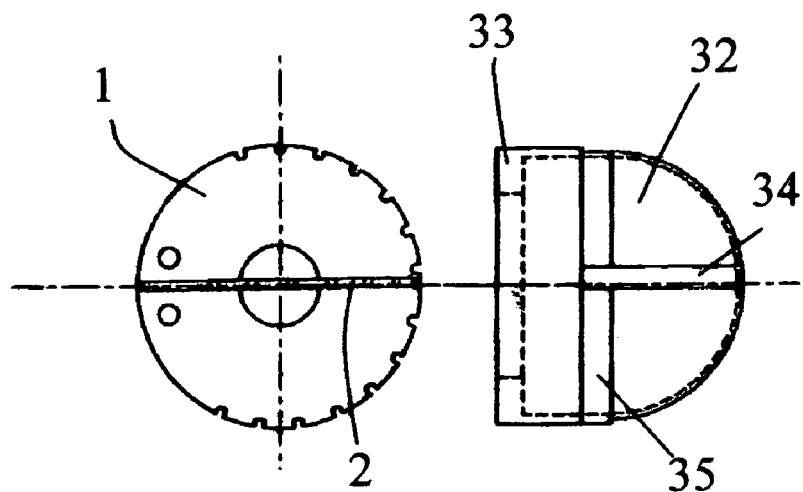
FIGS. 9a–9b show a cup for recovering the shavings before being mounted on the reamer.
Figure 10:
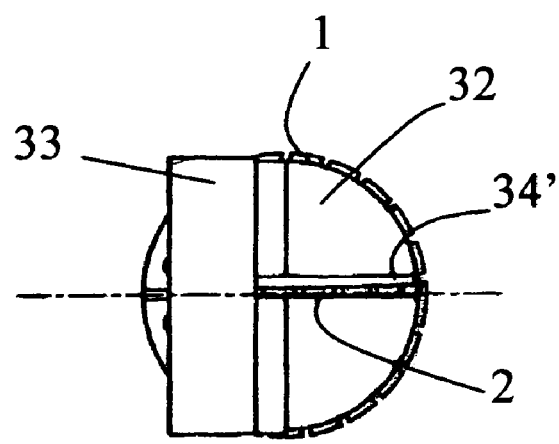
FIG. 10 shows the same cup mounted on the reamer.

The recovery devices are made up of a cup 32 in the shape of a hemispherical dome supported by a ring 33. The diameter of the cup 32 is slightly less than the diameter of the plates 1 and 2 and this cup has four splits 34 stretching according to the meridian levels at right angles to one another and over a part of the height of the ring 33, over a part 35 of the latter which has the same diameter as the cup 32. The width of the splits 34 is noticeably greater than the thickness of the plates 1 and 2 and these splits are asymmetrical in relation to the corresponding meridian plane, in such a way that when the cup 32 is mounted on the reamer (FIG. 10) the plates 1 and 2 cross the splits 34 leaving a split 34 behind the plates in relation to the reamer's direction of rotation, so as to allow the shavings to penetrate into the cup 32 through these splits 34. It will be noted that the reamer plates shown in FIGS. 9a and 9b and 10 are fitted with U-shaped teeth 50a, 50a', 50b, and 50b' which project over the surface of the cup 32.

Figure 11:
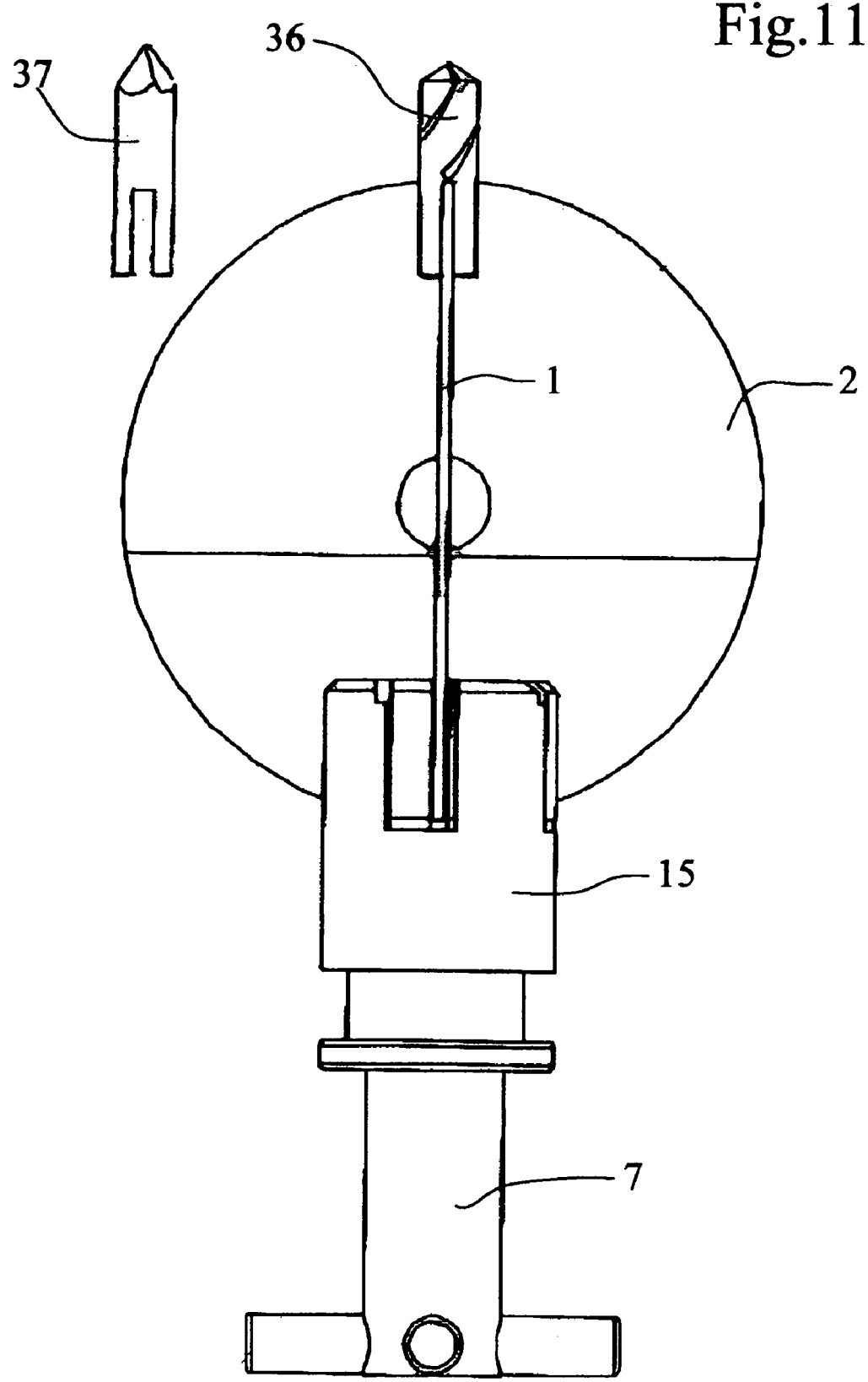
FIGS. 11a–11b show variants for point or centering stock production.

FIG. 11 illustrates a variation in which the two plates 1 and 2 are totally flat and form a cross at the end of the reamer. The reamer is fitted with a drill bit 36 fixed axially onto this cross. For this purpose, the bit 36 has two slots running crossways by means of which it is fitted onto the plates. The bit is laser welded onto the plates 1 and 2.

Figure 12:
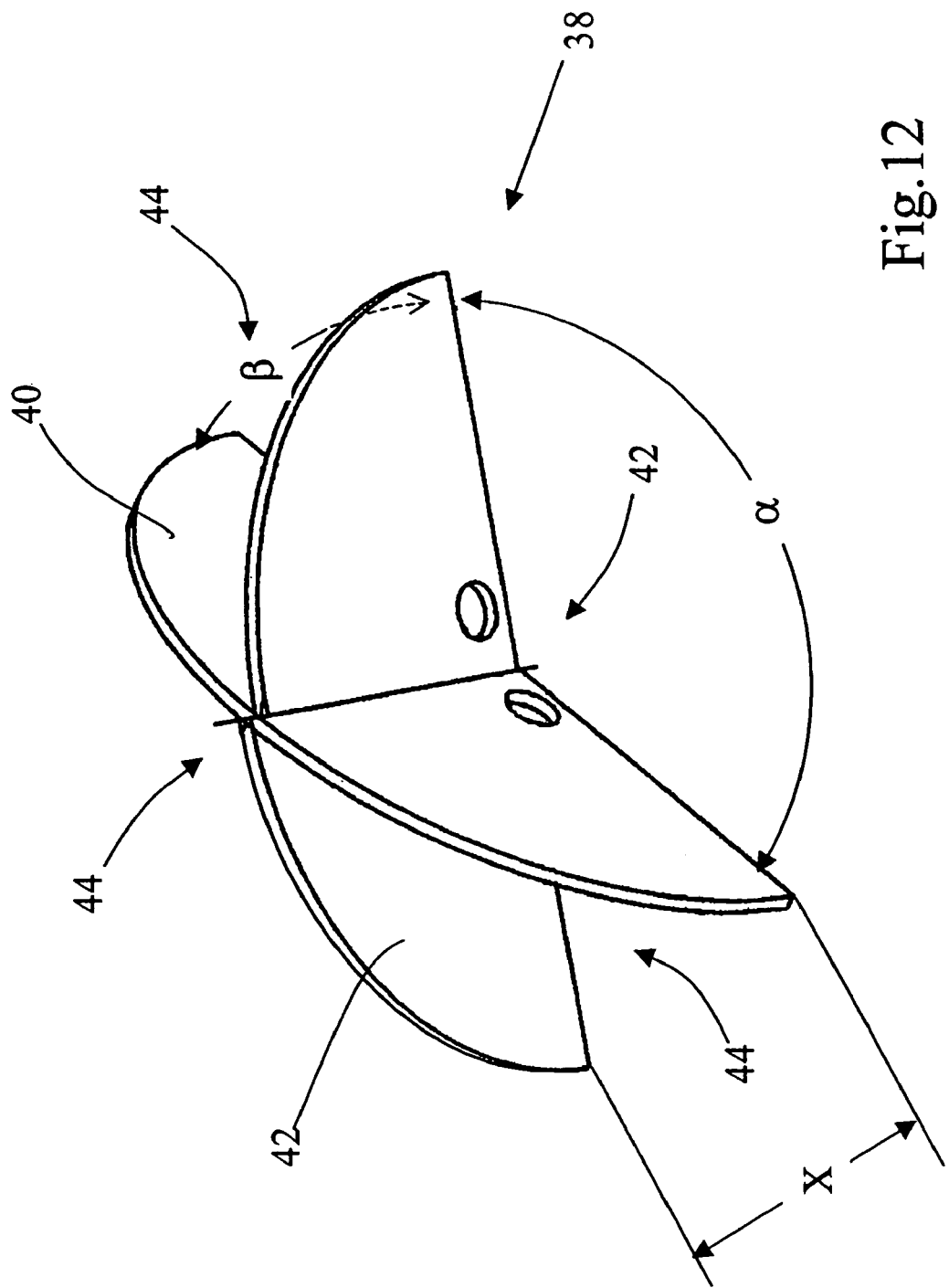
FIG. 12 shows an embodiment in which the plates are not equally spaced about the rotational axis.

FIG. 12 depicts a reamer 38 in which the plates 40 and 42 are spaced about the rotational axis so as to result in unequal spaces 44 between plates. The spaces 44 encompassed by angle β are smaller than the spaces encompassed by angle α, thus resulting in X and Y dimensions which are different.

Instead of a bit, a simple centre point or a trocar point 37 could be fitted.

A drill bit or a point could be fixed in the same way onto a reamer made up of three, five or more plates.

Figure 13:
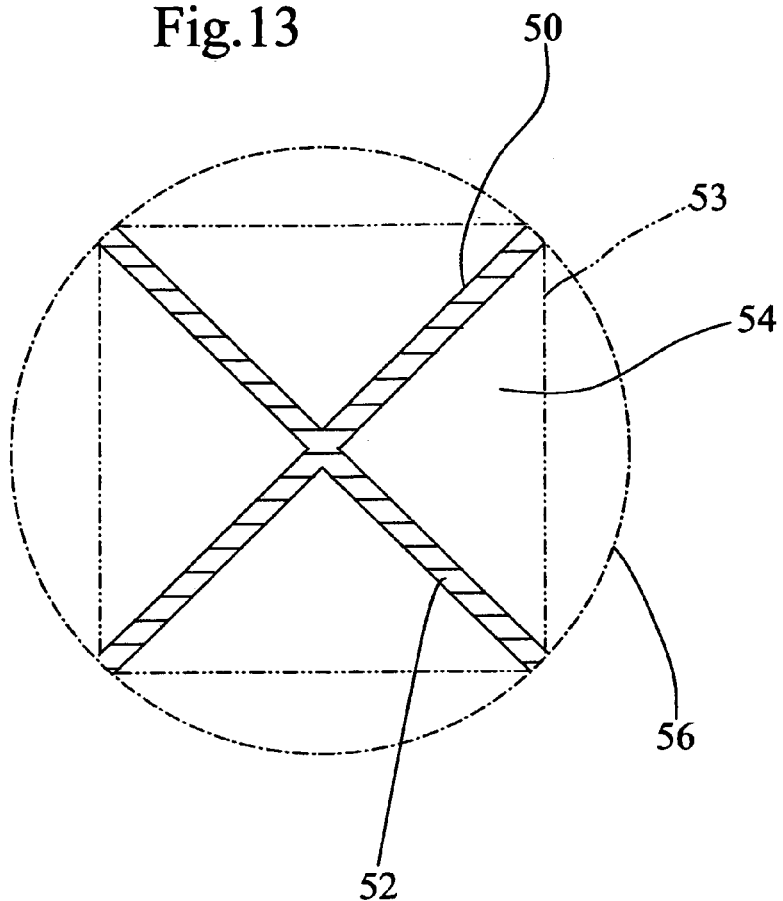
FIG. 13 shows the static profile area vs. the dynamic profile area of the invention.

FIG. 13 illustrates a cutting structure 50, made up of the two plates 1 and 2. When viewed statically and axially, the cutting structure 50 presents a two dimensional static profile area 52 in the form of a cross. The square 53 inscribed on the corners of this cross represents the minimum size of an incision which will allow passage of the reamer. The square 53 is therefore the effective profile seen by an incision upon insertion of the reamer into the bone socket and covers approximately 80% of the area of the circular profile area 54. When this static profile 52 is rotated during cutting, it sweeps out the circular profile area 54 inscribed by the phantom line circle 56.

Figure 14:
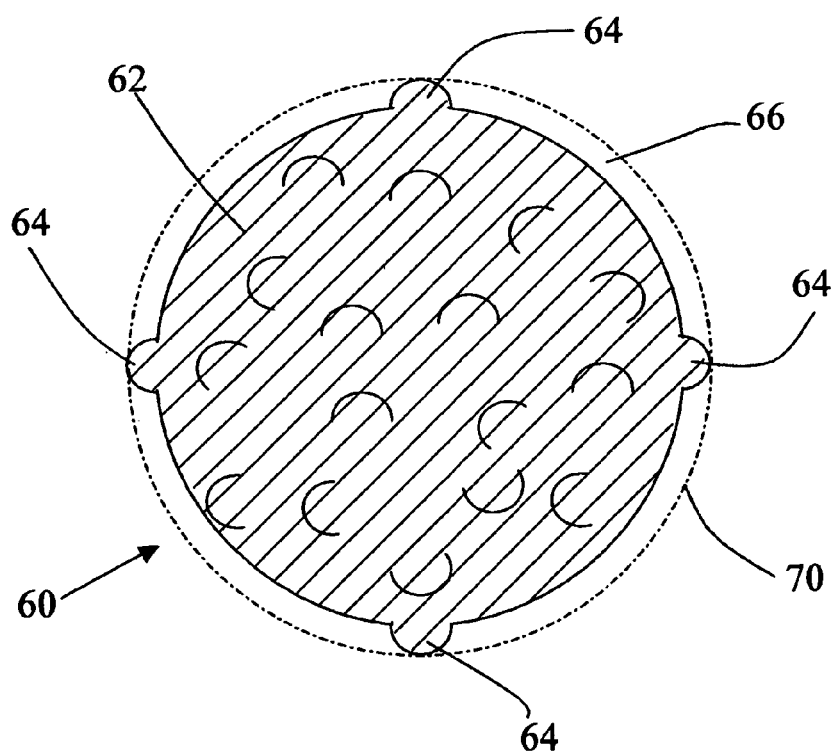
FIG. 14 shows the static profile area vs. the dynamic profile area of a prior art product.

FIG. 14 shows a conventional reamer 60, in which the static profile area 62 is essentially a circle with small protrusions 64 constituted of cutting divots. When rotated during cutting, the static profile area 62 sweeps out a dynamic profile area 66, inscribed by the phantom line 70, only insubstantially larger.

Thus, an advantage of having a substantially smaller static profile area 52 than dynamic profile area 54 is that the size of the incision required in order to receive the reamer is much smaller than that required for conventional reamers.

The invention is not limited to the modes of production described. Instead of the two fitted plates, the reamer could be made up of plates fixed radially on an axis, by means of welding, for instance. There do not have to be exactly four plates, but there must be at least one.

Whether these are plates fitted as shown or plates welded onto an axis, these plates could be of a different shape, for example a shape limited by a truncated or other form of case.

What is claimed is:

1. A tool holder for holding a surgical reamer during rotation about an axis of rotation of a reamer, the tool holder comprising a head (8) having an axis coincident with the axis of rotation of the reamer, the head being provided with two radially extending slots (10) each adapted to receive a plate (1, 2) of the reamer, the holder further comprising a retaining device (14, 15) having a component which is adapted to engage with a feature of a plate of the reamer, the feature being proximate the axis of rotation of the reamer in order to be capable of centrally retaining the plate in the respective slot.

2. The tool holder of claim 1, wherein the retaining device (14, 15) comprises a ball-detent arrangement.

3. The tool holder of claim 2, wherein the ball-detent arrangement comprises:
 (a) a ball guide (13) built into the head (8);
 (b) a ball (14) constrained to move within the ball guide (13); and
 (c) a ball locking component (15) which limits movement of the ball within the ball guide;
wherein when the ball locking component is engaged, the ball capable of being biased into a recess (18) of a plate (1, 2) of the reamer, thus locking the plate (1, 2) in the slot (10).

4. The tool holder of claim 3 wherein the length of the ball guide (13) is less than the diameter of the ball (14), and wherein the locking component (15) is biased to slide over an otherwise open end of the ball guide, so as to force the ball further into the ball guide and thus out an opposite end of the ball guide, so as to enter into a recess (18) of the plate (1,2) when a plate is installed.

5. The tool holder of claim 4, wherein the locking component (15) is a locking ring provided with fingers (16) extending parallel to the axis of the head, the locking ring (15) being biased by a spring (19) to nonrotatably slide along a cylindrical body (7) so that the fingers are biased to slide along a face adjacent to the ball guide so as to contact and push the ball (14) into the ball guide (13) and thus out the opposite end of the ball guide, and when a plate (1,2) is installed, into a recess (18) in the plate (1, 2), the locking ring able to occupy essentially two positions, one in which the finger is over an end of the ball guide containing the ball and the other in which the ball guide is unobstructed by the finger, permitting the ball, when the plate (1,2) is installed, to escape the recess (18) of the plate of the reamer.

6. The tool holder of claim 5, wherein the spring (19) of the locking ring (15) presses on a bearing ring (20) mounted in such a manner on the cylindrical body (7) that it may be freed by rotation and released to slide on the body, thus freeing the spring (19) and the locking ring (15).

7. The tool holder of claim 1, wherein an interface (9) is provided for fixing the tool holder to another tool holder.

* * * * *

UNITED STATES PATENT AND TRADEMARK OFFICE
CERTIFICATE OF CORRECTION

| | | |
|---|---|---|
| PATENT NO. | : 6,979,335 B2 | Page 1 of 1 |
| APPLICATION NO. | : 10/451481 | |
| DATED | : December 27, 2005 | |
| INVENTOR(S) | : Lechot | |

It is certified that error appears in the above-identified patent and that said Letters Patent is hereby corrected as shown below:

Column 1 after title on line 1, add the following header and paragraph:

-- CROSS REFERENCE TO RELATED APPLICATIONS
This application is the national stage entry of PCT/IB01/02675, filed December 21, 2001, which claims priority to CH 2500/00, filed December 21, 2000. --

Signed and Sealed this
Eighteenth Day of September, 2012

David J. Kappos
*Director of the United States Patent and Trademark Office*